(12) United States Patent
Lin et al.

(10) Patent No.: US 11,819,591 B2
(45) Date of Patent: Nov. 21, 2023

(54) IRON-BASED ALLOY ABSORBABLE AND IMPLANTABLE MEDICAL DEVICE FOR INTERNAL FIXATION

(71) Applicant: Biotyx Medical (Shenzhen) Co., Ltd., Shenzhen (CN)

(72) Inventors: Wenjiao Lin, Shenzhen (CN); Deyuan Zhang, Shenzhen (CN)

(73) Assignee: Biotyx Medical (Shenzhen) Co., Ltd., Shenzhen (CN)

( * ) Notice: Subject to any disclaimer, the term of this patent is extended or adjusted under 35 U.S.C. 154(b) by 740 days.

(21) Appl. No.: 15/775,137

(22) PCT Filed: Jun. 27, 2016

(86) PCT No.: PCT/CN2016/087292
§ 371 (c)(1),
(2) Date: May 10, 2018

(87) PCT Pub. No.: WO2017/113657
PCT Pub. Date: Jul. 6, 2017

(65) Prior Publication Data
US 2018/0326127 A1   Nov. 15, 2018

(30) Foreign Application Priority Data

Dec. 31, 2015  (CN) .......................... 201511032175.1

(51) Int. Cl.
*A61L 31/14*  (2006.01)
*A61L 31/06*  (2006.01)
(Continued)

(52) U.S. Cl.
CPC ............. *A61L 31/148* (2013.01); *A61L 17/10* (2013.01); *A61L 31/022* (2013.01); *A61L 31/06* (2013.01);
(Continued)

(58) Field of Classification Search
None
See application file for complete search history.

(56) References Cited

U.S. PATENT DOCUMENTS 6,306,426 B1 * 10/2001 Olejnik .................. A61L 27/54
604/890.1
2006/0115514 A1 * 6/2006 Gengrinovitch ........ A61L 27/54
607/2
(Continued)

FOREIGN PATENT DOCUMENTS

CN    102871715 A  *  1/2013
CN    103463686 A  * 12/2013
(Continued)

OTHER PUBLICATIONS

"Vitamin A Fact Sheet for Health Professionals", accessed online at https://ods.od.nih.gov/factsheets/VitaminA-HealthProfessional/, Feb. 14, 2020. (Year: 2020).*
(Continued)

*Primary Examiner* — Carlos A Azpuru
*Assistant Examiner* — Casey S Hagopian
(74) *Attorney, Agent, or Firm* — Maier & Maier, PLLC

(57) ABSTRACT

An iron-based alloy absorbable and implantable medical device for internal fixation. A substrate includes an iron-based alloy and degradable polymer. The mass ratio of the iron-based alloy to the degradable polymer is between 1:4 and 4:1. The weight-average molecular weight of the degradable polymer is between 150000 to 3000000, and the polydispersity index thereof is between 1 and 6. The device further includes antioxidants. The iron-based alloy is used as a load-bearing framework or reinforcement phase of the device. By adjusting the mass ratio of the iron-based alloy to the degradable polymer and the combination mode thereof, the corrosion rate of the iron-based alloy in the late period of the implantation is accelerated, and the quantity of
(Continued)

corrosion products poorly soluble in the iron-based alloy is reduced. Adding antioxidants to the device further reduces the quantity of the corrosion products poorly soluble in the iron-based alloy.

10 Claims, 1 Drawing Sheet

(51) Int. Cl.
*A61L 17/10* (2006.01)
*A61L 31/12* (2006.01)
*A61L 31/10* (2006.01)
*A61L 31/02* (2006.01)
*A61L 27/04* (2006.01)

(52) U.S. Cl.
CPC ............. *A61L 31/10* (2013.01); *A61L 31/128* (2013.01); *A61L 27/042* (2013.01)

(56) References Cited

U.S. PATENT DOCUMENTS

| | | | |
|---|---|---|---|
| 2006/0287676 A1* | 12/2006 | Prajapati | A61L 17/145 606/228 |
| 2009/0192594 A1* | 7/2009 | Borck | A61L 31/148 623/1.46 |
| 2009/0192595 A1* | 7/2009 | Nagura | A61L 27/58 623/1.46 |
| 2010/0076556 A1* | 3/2010 | Tomantschger | A61L 31/16 623/23.73 |
| 2011/0034996 A1 | 2/2011 | Borck | |
| 2011/0319978 A1 | 12/2011 | Schaffer et al. | |

FOREIGN PATENT DOCUMENTS

| | | | | |
|---|---|---|---|---|
| CN | 103877624 A | | 6/2014 | |
| CN | 104587534 A | | 5/2015 | |
| CN | 104720941 A | | 6/2015 | |
| JP | 08196616 A | * | 8/1996 | ............. A61L 31/06 |
| JP | 08196617 A | * | 8/1996 | ............. A61L 31/06 |
| WO | WO-2008013900 A2 | * | 1/2008 | ........... A61K 31/197 |
| WO | 2010/034098 A1 | | 4/2010 | |

OTHER PUBLICATIONS

Francis et al. "Iron and iron-based alloys for temporary cardiovascular applications", J Mater Sci: Mater Med (Feb. 2015) 26:138, pp. 1-16. (Year: 2015).*
"Meaning of Molecular Weight", Polymer Science Learning Center, accessed online on Apr. 15, 2021 at https://www.pslc.ws/macrog/weight.htm. (Year: 2021).*
"Calculating Molecular Weights", Polymer Science Learning Center, accessed online on Apr. 15, 2021 at https://www.pslc.ws/macrog/average.htm. (Year: 2021).*
Burg, "Poly($\alpha$-ester)s", Natural and Synthetic Biomedical Polymers, 2014, Chapter 6, pp. 115-121 (Year: 2014).*
Lin et al., Machine translation of CN 102871715 A, Jan. 2013. (Year: 2013).*
Machine translation of CN-103463686-A. (Year: 2013).*
Shikinami et al., Machine translation of JP-08196616-A, Aug. 6, 1996. (Year: 1996).*
"Molecular Weight", Jordi Labs, Accessed online on Mar. 6, 2023 at <https://jordilabs.com/wp-content/uploads/2017/02/White-Paper-Mw-Averages-Explanation.pdf>. (Year: 2023).*
International Search Report dated Oct. 13, 2016 of corresponding International Application No. PCT/CN2016/087292; 8 pgs.

* cited by examiner

IRON-BASED ALLOY ABSORBABLE AND IMPLANTABLE MEDICAL DEVICE FOR INTERNAL FIXATION

FIELD

The present application belongs to the field of absorbable implantable medical devices, and more particularly relates to an iron-based alloy absorbable and implantable medical device for internal fixation.

BACKGROUND

Fracture healing time varies with different injured parts, different severities of injuries and even different therapies, and generally lasts 2 to 6 months, which requires that an implantable medical device for internal fixation should have certain initial mechanical properties. For example, the initial bending strength of a bone screw generally needs to be 350 MPa or higher, and the tensile strength of a suture needs to be 400 MPa or higher. Materials for manufacturing the implantable medical device for internal fixation for wound healing at the present mainly include a permanent metal such as stainless steel, a titanium-based alloy and a cobalt-based alloy, and an absorbable material such as a polymer and a magnesium-based alloy, wherein the permanent metal has excellent mechanical properties and biocompatibility; and after an injured bone is healed, the permanent metal will stay in a human body for a long time, which may cause a potential long-term biological risk, but taking out of this permanent metal will increase the pain and the economical burden on a patient, and also may possibly cause secondary injury (for example, a loose thread is broken and remains in the body).

The absorbable polymer, such as polylactic acid and polycaprolactone, has good biocompatibility. Plenty of clinical data of absorbable polymer have been accumulated. Generally, within a certain range, higher molecular weight and crystallinity of the polymer make its comprehensive mechanical properties higher, but the polymer is dissolved in an organic solvent more difficultly. Therefore, only after being heated into a flowing melt, the polymer may be prepared into a finished product through die pressing, injection molding, drawing or extrusion forming. A structure, such as an absorbable polymer coating of the medical device, having a low requirement of mechanical properties, is usually formed by dissolving a low molecular weight polymer in an organic solvent and then applied to the surface or inside of the medical device. A processing method of a polymer with a high molecular weight generally includes melting and then processing forming, so that the polymer with the high molecular weight is applicable to manufacturing of an implantable medical device for internal fixation with certain mechanical strength for wound healing. Although the bending strength of an absorbable bone screw manufactured by polylactic acid with a high molecular weight may reach 150 MPa or higher, compared with a conventional permanent metal material, it has shortcomings as follows: due to its mechanical properties, the absorbable bone screw is generally only applicable to fixation of cancellous bones, articular bones or bones with less activity of various non-bearing parts to prevent a failure of the implantable medical device resulted from overstress or frequent activities; degradation of the polylactic acid will generate an acidic environment, which easily leads to relatively severe inflammatory reactions occurring in an implanted part; and furthermore, the radiopacity is insufficient. All these shortcomings restrict application of an absorbable polymer-based and implantable medical device for internal fixation.

The bending strength of a magnesium-based alloy and implantable medical device for internal fixation may reach about 300 MPa, but the mechanical properties of the magnesium-based alloy still may not reach the level of a permanent metal implanted material, so that the magnesium-based alloy and implantable medical device for internal fixation is still only applied to non-bearing positions and positions with less activities at the present, for example, to internal fixation of ossicles and sclerites, and the clinical application range is limited; and in addition, the magnesium-based alloy is corroded quickly, so that the implantable medical device will lose its effective supporting and fixing effects too early, and the corrosion of the magnesium-based alloy will increase the local pH of the implanted part, which may produce a harmful effect on bone growth and easily lead to poor synosteosis.

An absorbable iron-based alloy may have the mechanical properties close to those of permanent stainless steel, a cobalt-chromium alloy and a titanium alloy, and have improved mechanical properties compared with the absorbable polymer and the magnesium-based alloy, but its corrosion is slow. In CN104587534, it is disclosed that the corrosion of the iron-based alloy may be obviously accelerated in the acidic microenvironment formed by degradation of a macromolecular material such as degradable polyester, so that the corrosion cycle of the iron-based alloy is obviously shortened, but corrosion products generated by oxygen absorption corrosion of the absorbable iron-based alloy are generally insoluble ferric hydroxides or oxides. In soft and hard tissues in the body, these insoluble ferric corrosion products are possibly metabolized and absorbed by organs for several years or even longer; and although they have extremely good biocompatibility, their long-term existence aggravates the burden on tissues for the metabolization of corrosion products. Therefore, it is necessary to reduce the insoluble corrosion products of the iron-based alloy absorbable and implantable medical device for internal fixation while keeping the mechanical properties.

SUMMARY

The present application provides an iron-based alloy absorbable and implantable medical device for internal fixation which has relatively high initial mechanical properties on the premise of reducing the amount of an iron-base alloy substrate, and in the late period of the implantation, the amount of insoluble corrosion products of an iron-based alloy is reduced, thereby relieving the burden on tissues for the metabolization of corrosion products.

An iron-based alloy absorbable and implantable medical device for internal fixation is provided. A substrate of the iron-based alloy absorbable and implantable medical device for internal fixation includes an iron-based alloy and a degradable polymer. The mass ratio of the iron-based alloy to the degradable polymer is between 1:4 and 4:1; and the weight-average molecular weight of the degradable polymer is more than or equal to 150,000 and less than or equal to 3,000,000, and the polydispersity index is more than or equal to 1 and less than or equal to 6.

The mass ratio of the iron-based alloy to the degradable polymer may be between 1:4 and 1:1 in one exemplary embodiment.

The iron-based alloy absorbable and implantable medical device for internal fixation further includes an antioxidant which is at least one of butyl hydroxy anisole, butylated hydroxytoluene, tertiary butylhydroquinone, propylgallate, vitamin A, carotenoid, ubiquinone, glutathione, water-soluble polyphenol, tocopherol, sodium tripolyphosphate, sodium ascorbate, lipoic acid salt and scorbic palmitate, and the water-soluble polyphenol is selected from the group consisting of resveratrol and flavonoid.

The degradable polymer includes degradable polyester, or a mixture of the degradable polyester and at least one of degradable polyanhydride, degradable polyamino acid and degradable polyphosphate ester, or a copolymer of at least one monomer forming the degradable polyester and at least one monomer forming the degradable polyanhydride, the degradable polyamino acid or the degradable polyphosphate ester.

The degradable polyester is selected from the group consisting of polylactic acid, polyglycolic acid, poly(ethylene succinate), polycaprolactone, polyhydroxyalkanoate, polyethylene glycol adipate, a polylactic acid-glycolic acid copolymer and a polyhydroxybutyrate-pentanoate copolymer, or a physical blend of at least two of the polylactic acid, the polyglycolic acid, the poly(ethylene succinate), the polycaprolactone, the polyhydroxyalkanoate, the polyethylene glycol adipate, the polylactic acid-glycolic acid copolymer and the polyhydroxybutyrate-pentanoate copolymer, or a copolymer of at least two monomers of monomers forming the degradable polyester; the degradable polyanhydride is any one of crosslinked polyanhydride, aromatic polyanhydride, fatty acid anhydride, heterocyclic polyanhydride, poly-acyl anhydride, polyamide anhydride and phosphorus-containing anhydride, or a physical blend of at least two of the crosslinked polyanhydride, the aromatic polyanhydride, the fatty acid anhydride, the heterocyclic polyanhydride, the poly-acyl anhydride, the polyamide anhydride and the phosphorus-containing anhydride; and the degradable polyamino acid is at least one of polyglycine, poly-methionine, polythionine and polyaspartic acid.

The iron-based alloy is pure iron or an iron-based alloy with a carbon content less than or equal to 2.11 weight percent.

The iron-based alloy absorbable and implantable medical device for internal fixation is a bone screw or a suture.

Compared with the prior art, the present application takes the iron-based alloy as a load-bearing framework or a reinforcement phase of the device, so that the device has the high initial mechanical properties on the premise of reducing the amount of the iron-based alloy substrate; by the adjusting the mass ratio of the iron-based alloy to the degradable polymer and a combination mode thereof, when the corrosion rate of the iron-based alloy substrate in the late period of the implantation is accelerated, the amount of insoluble corrosion products of the iron-based alloy is reduced, and the burden on the tissues for the metabolization of the corrosion products is relieved; and the adding of the antioxidant further reduces the amount of the insoluble corrosion products of the iron-based alloy.

DETAILED DESCRIPTION

Figure 1:
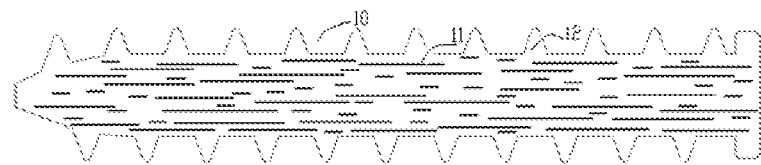
FIG. 1 is a schematic diagram of a structure of a bone screw manufactured in Embodiment 1.

For the purpose of facilitating the understanding of the present application, a more comprehensive description will be made below to the present application with reference to relevant accompanying drawings. In these drawings, an exemplary embodiment of the present application is shown. However, the present application may be implemented in many different ways, but not limited to the embodiments described herein. On the contrary, the objective of providing these embodiments is to make contents disclosed in the present application more thorough and comprehensive.

Unless otherwise defined, all technical and scientific terms used in this text are the same as meanings of general understandings of technical persons skilled in the art of the present application. The terms used in the description herein are merely descriptive of specific embodiments, but not intended to limit the present application.

A matrix material of an iron-based alloy absorbable and implantable medical device for internal fixation of the present application includes an iron-based alloy and a degradable polymer. The mass ratio of the iron-based alloy to the degradable polymer is between 1:4 and 4:1, so that the device has high initial mechanical properties on the premise of reducing the amount of iron-based alloy substrate, and may be corroded and degraded faster in the late period of implantation; and moreover, the amount of insoluble corrosion products is reduced and the burden on the tissues for the metabolization of the corrosion products is relieved.

There are two primary ways to reduce the amount of the insoluble corrosion products of the device: the first way is to reduce the amount of the iron-based alloy substrate, and the second way is to reduce the mass percent of the insoluble corrosion products of the iron-based alloy, namely to increase the mass percent of soluble iron in the corrosion products of iron-based alloy.

Combinations of an iron-based alloy and degradable polymer composite include:

the iron-based alloy is distributed into the degradable polymer by means of a solid or hollow bristle shape, filament shape or rod shape, an irregular stent or a mesh; or the iron-based alloy and the degradable polymer are respectively prepared into layered substances, and the iron-based alloy layer and the polymer layer are alternated with each other; or the iron-based alloy is stranded on a degradable polymer filament in the form of a filament; or the iron-based alloy has a groove, a pore, a gap or a hollow inner cavity, and the groove, the pore, the gap or the hollow inner cavity is filled with the degradable polymer.

By the adoption of the above-mentioned combinations of the iron-based alloy and the degradable polymer, the initial mechanical properties which is close to or equivalent to that of a device made of a permanent metal material (such as stainless steel, cobalt-chromium alloy and titanium-based alloy) may be obtained, and the amount of the iron-based alloy substrate may be reduced at the same time, so that the amount of the possibly generated insoluble corrosion products is reduced.

The degradable polymer includes degradable polyester, or a mixture of the degradable polyester and at least one of degradable polyanhydride, degradable polyamino acid and degradable polyphosphate ester, or a copolymer of at least one monomer forming the degradable polyester and at least one monomer forming the degradable polyanhydride, the degradable polyamino acid or the degradable polyphosphate ester.

The degradable polyester is selected from the group consisting of polylactic acid, polyglycolic acid, poly(ethylene succinate), polycaprolactone, polyhydroxyalkanoate, polyethylene glycol adipate, a polylactic acid-glycolic acid copolymer and a polyhydroxybutyrate-pentanoate copolymer, or a physical blend of at least two of the polylactic acid, the polyglycolic acid, the poly(ethylene succinate), the polycaprolactone, the polyhydroxyalkanoate, the polyethylene glycol adipate, the polylactic acid-glycolic acid copolymer and the polyhydroxybutyrate-pentanoate copolymer, or a copolymer of at least two monomers of monomers forming the degradable polyester; the degradable polyanhydride is selected from the group consisting of crosslinked polyanhydride, aromatic polyanhydride, fatty acid anhydride, heterocyclic polyanhydride, poly-acyl anhydride, polyamide anhydride and phosphorus-containing anhydride, or a physical blend of at least two of the crosslinked polyanhydride, the aromatic polyanhydride, the fatty acid anhydride, the heterocyclic polyanhydride, the poly-acyl anhydride, the polyamide anhydride and the phosphorus-containing anhydride; and the degradable polyamino acid is at least one of polyglycine, poly-methionine, polythionine and polyaspartic acid.

After the iron-based alloy absorbable and implantable medical device for internal fixation is implanted into a human body, the iron-based alloy substrate is gradually corroded in a physiological solution to generate a primary corrosion product $Fe^{3+}$ or $Fe^{2+}$; and the $Fe^{3+}$ or $Fe^{2+}$ then reacts with $OH^-$ in the environment to generate the insoluble corrosion products such as $Fe(OH)_2$ and $Fe(OH)_3$. The degradable polyester, the degradable polyanhydride, the degradable polyamino acid and the degradable polyphosphate ester may release hydrogen ions after being degraded, which may effectively inhibit the reaction between the $Fe^{3+}$ or $Fe^{2+}$ and the $OH^-$; in addition, complex ions (ligands) generated by the degradation of the degradable polyester, the degradable polyanhydride, the degradable polyamino acid and the degradable polyphosphate ester undergo complexing reaction with the $Fe^{3+}$ or $Fe^{2+}$ more preferentially than the $OH^-$ in the environment to generate a stable soluble iron complex, thereby further reducing or preventing generation of the insoluble corrosion products, which are generated by the reaction between the $Fe^{3+}$ or $Fe^{2+}$ and the $OH^-$ in the environment. If the mass ratio of the iron-based alloy to the degradable polymer in the device is smaller, the mass ratio of generated iron in the form of ions or a soluble iron complex to iron in corrosion products of the iron-based alloy is larger, but if the mass ratio of the iron-based alloy to the degradable polymer is smaller, the mechanical properties of the device is lower. Therefore, the mass ratio of the iron-based alloy to the degradable polymer of the present application is between 1:4 and 4:1, for example 1:4 and 1:1, which enables the device to obtain ideal mechanical properties and also reduces the amount of the insoluble corrosion products.

The iron-based alloy absorbable and implantable medical device for internal fixation also includes an antioxidant. The antioxidant is selected from the group consisting of butyl hydroxy anisole, butylated hydroxytoluene, tertiary butylhydroquinone, propylgallate, vitamin A, carotenoid, ubiquinone, glutathione, water-soluble polyphenol, tocopherol, sodium tripolyphosphate, sodium ascorbate, lipoic acid salt and scorbic palmitate, and the water-soluble polyphenol is selected from the group consisting of resveratrol and flavonoid.

The surface of the iron-based alloy may be coated with the antioxidant; when the iron-based alloy has a gap, a groove or an inner cavity, the gap, the groove or the inner cavity also is filled with the antioxidant; and in addition, the antioxidant may be dispersed in the degradable polymer.

Although the insoluble corrosion products are extremely low in solubility in a physiological environment, there are still a few of ions entering the solution; in addition, the ions entering the solution may be settled down on the surfaces of solids; when the insoluble corrosion products reach a dissolution equilibrium, an equilibrium constant is called a solubility product constant (precipitation equilibrium constant), namely a solubility product. The solubility product of an insoluble corrosion product $Fe(OH)_3$ generated by $Fe^{3+}$ and $OH^-$ is much less than that of an insoluble corrosion product $Fe(OH)_2$ generated by $Fe^{2+}$ and $OH^-$, namely the amount of $Fe^{3+}$ entering the solution is much less than that of $Fe^{2+}$ entering the solution. Therefore, the corrosion product of ferric iron is more difficult to metabolize in the body; and adding of the antioxidant into the iron-based alloy absorbable and implantable medical device for internal fixation may inhibit transformation from $Fe^{2+}$ to $Fe^{3+}$, thereby reducing generation of the insoluble corrosion products with ferric iron and improving the solubility of iron.

The iron-based alloy absorbable and implantable medical device for internal fixation also includes a complexing agent. The complexing agent is a monodentate ligand and/or a polydentate ligand. The monodentate ligand contains a single coordination group. The polydentate ligand contains at least two coordination groups, each of which is hydroxyl on polycyclic aromatic hydrocarbon, sulfydryl (—SH),

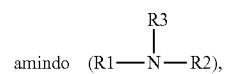

a hetero aromatic group, nitroso (O=N—), carbonyl

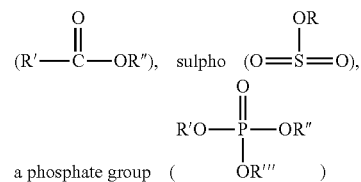

and an organic phosphine group

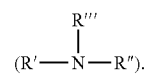

The hydroxyl on the polycyclic aromatic hydrocarbon is a phenolic hydroxyl group. The hetero aromatic group is selected from the group consisting of

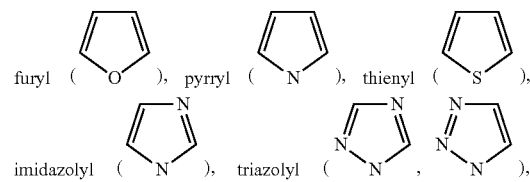

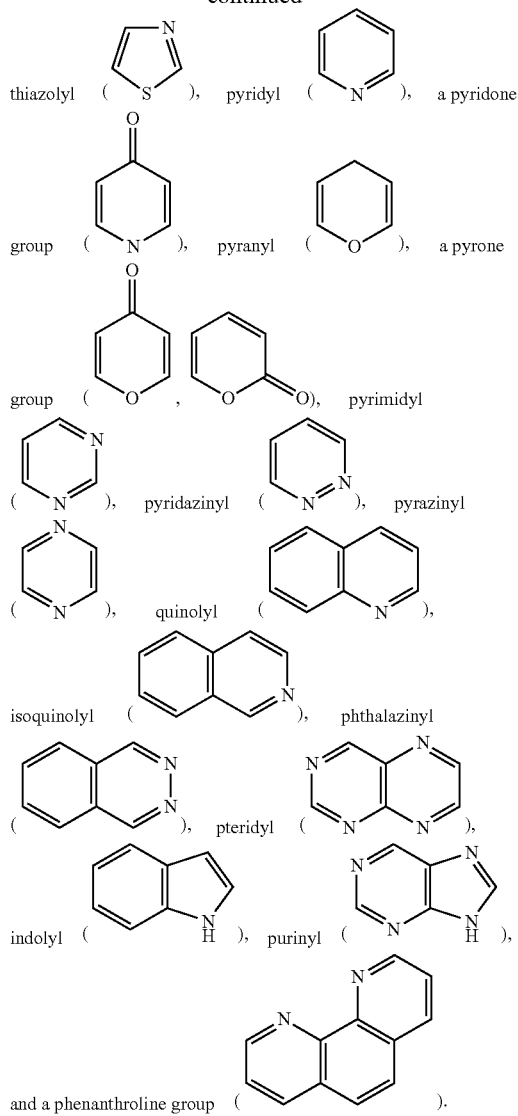

The monodentate ligand is selected from the group consisting of gluconic acid, glucoheptonic acid, glycolic acid and derivatives or salts thereof.

The polydentate ligand containing a hydroxy group on a polycyclic aromatic hydrocarbon is selected from the group consisting of 8-hydroxyquinoline, 8-hydroxyquinaldine and 4,5-dioxybenzene-1,3-sodium disulfonate and 4-[3,5-bis-hydroxyphenyl-1H-1,2,4-triazole]-benzoic acid (deferasirox); the sulfydryl-containing polydentate ligand is selected from the group consisting of 8-mercaptoquinoline, mercaptoacetic acid and 5-methyl-2-methyl mercaptobenzoate; the amido-containing polydentate ligand is selected from the group consisting of ethidene diamine, triethylene tetramine, ethylenediamine tetraacetic acid, ethylene diamine tetraacetic acid tetrasodium and N'-[5-[[4-[[5-(acetyl hydroxylamine)amyl]ammonia]-1,4-dioxo butyl] hydroxylamine]amyl]-N-(5-amido amyl)-N-hydroxyl succinamide (deferoxamine); the hetero aromatic group-containing polydentate ligand is selected from the group consisting of phenanthroline, dipyridyl, porphyrin, porphin, chlorophyll, hemoglobin and 1,2-dimethyl-3-hydroxyl-4-pyridone (deferiprone); the nitroso-containing polydentate ligand is selected from the group consisting of 1-nitroso-2-naphthol and 1-nitroso-2-naphthol-6-sodium sulfonate; the carbonyl-containing polydentate ligand is selected from the group consisting of polybasic carboxylic acid and salt thereof, anhydride, ester, amide, polycarboxylic acid and polyanhydride; the sulpho-containing polydentate ligand is selected from the group consisting of sulfosalicylic acid and 8-hydroxyquinoline-5-sulphonic acid; the phosphate group-containing polydentate ligand is selected from the group consisting of pyrophosphoric acid, tripolyphosphoric acid, hexametaphosphoric acid, polyphosphoric acid, sodium pyrophosphate, sodium hexametaphoshpate and ammonium polyphosphate; the organic phosphine group-containing polydentate ligand is selected from the group consisting of potassium diethylenetriamine pentamethylene phosphonate and sodium ethylenediamine tetramethylene phosphonate; the carbonyl-containing polydentate ligand is further selected from the group consisting of oxalic acid, tartaric acid, malic acid, succinic acid, oxaloacetic acid, fumaric acid, maleic acid, citric acid, nitrilotriacetic acid, diethylene triamine pentacarboxylic acid, alginic acid, glutamic acid, aspartic acid, ornithine, lysine, potassium citrate, calcium citrate, monoglyceride citrate, acetylsalicylic acid, sulpho salicylamide, polyaspartic acid, polyglutamic acid, poly-ornithine, polylysine and polymaleic anhydride.

The surface of the iron-based alloy may be coated with the complexing agent; when the iron-based alloy has a gap, a groove or an inner cavity, the gap, the groove or the inner cavity of the iron-based alloy also may be filled with the complexing agent; and in addition, the complexing agent also may be dispersed in the degradable polymer.

In a physiological environment, the complexing agent may provide lone pair electrons or pi electrons for complex reaction with $Fe^{2+}$ and/or $Fe^{3+}$ to generate a water-soluble iron complex. The water-soluble iron complex may be metabolized/absorbed by an organism faster than the insoluble solid corrosion products of the iron-based alloy, has higher stability than that of $Fe(OH)_2$ and/or $Fe(OH)_3$, and would not be turned into insoluble $Fe(OH)_2$ and/or $Fe(OH)_3$ in the physiological solution.

The iron-based alloy absorbable and implantable medical device for internal fixation also includes a degradable adhesive with good biocompatibility. The degradable adhesive is selected from the group consisting of a polyester hot melt adhesive, a polyamide hot melt adhesive, starch, cyclodextrin and lignin, or is a copolymer of at least two of monomers forming the polyester hot melt adhesive, the polyamide hot melt adhesive, the starch, the cyclodextrin and the lignin.

In order to investigate a corrosion condition of the iron-based alloy absorbable and implantable medical device for internal fixation, an in-vitro corrosion acceleration test on the device is carried out in the present application: under a condition of 80° C., after the device is soaked in 100 mL of a PBS (Phosphate Buffer Solution) for corrosion for three weeks, a soluble corrosion product generated by corrosion of the iron-based alloy is fully dissolved in the PBS, and the soaking solution is filtered with a water-based film with an aperture of 0.22 μm; then an AAS (Atomic Absorption Spectrometer) is adopted to test the concentration c of an iron element dissolved in filtrate; the mass m1 of soluble iron dissolved in the PBS is equal to cV, wherein V is the volume of the solution; the device is taken out, and then is cleaned and weighed after being subjected to iron rust removal, thus a weight loss Δm of the iron-based alloy portion is obtained, namely the mass of the iron in corrosion products of the iron-based alloy; the mass percent W of the soluble iron in corrosion products of the iron-based alloy is as shown in Formula (1):

$$W=m_1/\Delta m \times 100\%  \quad \text{Formula(1)},$$

where W represents the mass percent of the soluble iron corrosion product in corrosion products of the iron-based alloy;
$m_1$ represents the mass of the soluble iron in the PBS; and
$\Delta m$ represents the mass of the iron in corrosion products of the iron-based alloy.

The larger W indicates more soluble corrosion products formed in the corrosion products of the iron-based alloy, namely fewer insoluble corrosion products, and smaller burden on tissue metabolization.

The present application investigates the initial mechanical properties of the iron-based alloy absorbable and implantable medical device for internal fixation by testing the bending strength or the tensile strength. The initial bending strength of the implantable medical device for internal fixation manufactured in the present application is not less than 350 MPa, and the tensile strength is not less than 400 MPa, so that it is deemed that the implantable medical device for internal fixation of the present application meets the standard for an implantable medical device for internal fixation for a load-bearing position.

In this present application, a universal material tester C43.504 of the MTS Company is adopted to test the three-point bending strength of a test sample according to a test standard YBT 5349-2006 for metal material bending mechanical property.

In this present application, the universal material tester C43.504 of the MTS Company is adopted to test the tensile strength of the test sample according to a tensile test standard GBT 228.1-2010.

It should be noted that in all the exemplary embodiments below, a normal fluctuation of the performance of a product within a designed allowable range and a system error unavoidably introduced by test methods may lead to fluctuations of the actually detected mass percent of the soluble iron corrosion product in corrosion products of the iron-based alloy within a certain range.

Embodiment 1

Low-alloy high-strength steel with the alloy content less than 6 weight percent is cast into a blank, then the blank is cold-drawn to form an ultrafine steel wire with a diameter of 0.2 mm, and then thermal treatment is carried out; and the steel wire with a diameter of 0.2 mm which is prepared by the above steps is cut into small sections with different lengths, and the small sections are coated with triammonium citrate serving as a complexing agent.

A blank of polylactic acid-glycolic acid (PLGA) with the weight-average molecular weight of 1,200,000 and the polydispersity index of 1.1 is heated to a molten state, and vitamin A serving as an antioxidant is dispersed into the PLGA blank; the steel wire sections which is treated in the above steps are directionally arrayed and then are added into the molten PLGA blank so as to be used as a reinforcement phase; after condensation and solidification, the molten PLGA blank is extruded into a rod; and the rod is machined into a bone screw 10 as shown in FIG. 1, wherein the mass ratio of the steel wire reinforcement phase 11 to a polylactic acid-glycolic acid phase 12 is 20:80.

The initial bending strength of the material manufactured for the bone screw in this embodiment is 350 MPa, and after accelerated corrosion in vitro for three weeks, the mass percent of the soluble iron in corrosion products of the iron-based ally is 45 weight percent.

Embodiment 2

Low-alloy high-strength steel with the alloy content less than 6 weight percent is prepared into a blank by adopting a method of powder metallurgy, and then the blank is hot-rolled into a steel wire rod which is then cold-drawn into a hollow steel wire; a core portion of the hollow steel wire is filled with ascorbic palmitate serving as an antioxidant; and multiple strands of steel wires are stranded into a steel strand, and a complexing agent layer of hydroximic acid deferoxamine is prepared on the surface of the steel strand.

Figure 2:
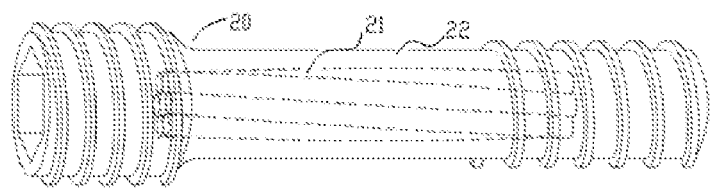
FIG. 2 is a schematic diagram of a structure of a bone screw manufactured in Embodiment 2.

Polylactic acid (PLA) with the weight-average molecular weight of 3,000,000 and the polydispersity index of 1.2 and polylactic acid-methionine with the molecular weight of 250,000 are prepared into a blend blank; the steel strand prepared in the above steps is put into the blend blank containing molten PLA and polylactic acid-methionine, and is used as a reinforcement phase; and after being solidified, the blend is machined into a pressure screw 20 as shown in FIG. 2, wherein the mass ratio of the steel strand reinforcement phase 21 to the blend phase 22 containing PLA and polylactic acid-methionine is 30:70. The initial bending strength of the material manufactured for the pressure screw in this embodiment is 450 MPa, and after accelerated corrosion in vitro for three weeks, the mass percent of the soluble iron in corrosion products of the iron-based ally is 35 weight percent.

Embodiment 3

Low-alloy high-strength steel with the alloy content less than 6 weight percent is prepared into a blank by adopting a method of powder metallurgy, and then is hot-rolled into a steel wire rod which is then cold-drawn into a hollow steel wire; the hollow steel wire is filled with acetylsalicylic acid serving as a complexing agent; and multiple strands of steel wires are stranded and then are woven into a two-dimensional mesh, and a hydroxyapatite layer is prepared on the surface of the two-dimensional mesh and then is coated with ubiquinone serving as an antioxidant.

After a blank of polylactic acid with the weight-average molecular weight of 2,000,000 and the polydispersity index of 1.5 is heated to a molten state, multiple layers of two-dimensional meshes are added into the blank; after the blank and the meshes are uniformly mixed, the mixture is subjected to condensation and solidification, and then is machined into a bone screw; and the extending directions of all the two-dimensional meshes in the bone screw are consistent, and the mass ratio of the two-dimensional meshes to the polylactic acid blank is 25:75.

The initial bending strength of the material manufactured for the bone screw in this embodiment is 400 MPa, and after accelerated corrosion in vitro for three weeks, the mass percent of the soluble iron in corrosion products of the iron-based ally is 35 weight percent.

Embodiment 4

A blank of as-cast pure iron is hot-rolled into a steel wire rod which is then cold-drawn into a hollow iron wire; an inner cavity of the iron wire is filled with sodium gluconate serving as a complexing agent and sodium tripolyphosphate serving as an antioxidant; a blank of lactic acid-phosphate copolymer with the weight-average molecular weight of 500,000 and the polydispersity index of 5 is obtained in a way of melt polymerization, and then is drawn into wires; the copolymer and multiple strands of iron wires are stranded to form a strand with a larger wire diameter; cyclodextrin is added into the strand, and pressing molding is carried out, thus an absorbable suture is manufactured. The mass ratio of the iron wires to the lactic acid-phosphate copolymer in the suture is 50:50.

The initial bending strength of the suture manufactured in this embodiment is 400 MPa, and after accelerated corrosion in vitro for three weeks, the mass percent of the soluble iron in corrosion products of the iron-based ally is 25 weight percent.

Embodiment 5

Figure 3:
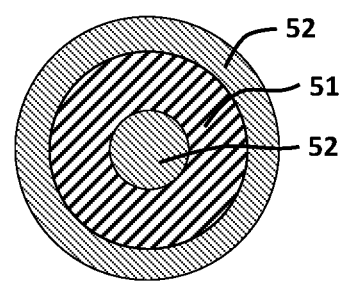
FIG. 3 is a schematic diagram of a section of a composite rod which is used for manufacturing a bone screw in Embodiment 5.

Medium carbon steel with a carbon content of 0.3 weight percent is prepared into a blank through casting, and then the blank is further subjected to thermal treatment; the medium carbon steel and a blank of polylactic acid (PLA) which is dispersed with sodium ascorbate with a weight-average molecular weight of 2,600,000 and a polydispersity index of 2 are coextruded to prepare a multilayer compound rod having a section as shown in FIG. 3, wherein 51 represents medium carbon steel layer and 52 represents polymer layer. A polyester hot melt adhesive is added between the medium carbon steel layer 51 and the polymer layer 52, and then the rod is prepared into a solid bone screw by machining, wherein the mass ratio of the medium carbon steel to PLA is 50:50.

The initial bending strength of the material manufactured for the bone screw in this embodiment is 450 MPa, and after accelerated corrosion in vitro for three weeks, the mass percent of the soluble iron in corrosion products of the iron-based ally is 15 weight percent.

Embodiment 6

Low-alloy high-strength steel with an alloy content less than 6 weight percent is cast into a blank, and then the blank is hot-rolled into a steel wire rod which then is cold-drawn into a hollow steel wire; an inner cavity of the steel wire is filled with sodium gluconate serving as a complexing agent; a polylactic acid (PLA)-maleic anhydride copolymer with the weight-average molecular weight of 3,000,000 and the polydispersity index of 1.2 is drawn into a wire; butyl hydroxyl anisole serving as an antioxidant is also dispersed in the copolymer; the steel wire and the copolymer wire are stranded together into a composite strand; in the process of manufacturing the strand, a polyamide hot melt adhesive is added between the steel wire and the copolymer wire; and finally the strand is machined into a pressure screw. The mass ratio of the steel wire to the copolymer wire in the pressure screw is 65:35.

The initial bending strength of the pressure screw in this embodiment is 500 MPa, and after accelerated corrosion in vitro for three weeks, the mass percent of the soluble iron in corrosion products of the iron-based ally is 15 weight percent.

Embodiment 7

Low-carbon low-alloy steel with the carbon content of 0.1 weight percent is prepared into a blank by powder metallurgy, and then the blank is further subjected to thermal treatment; polylactic acid with a weight-average molecular weight of 2,000,000 and a polydispersity index of 1.8 and a polymaleic anhydride-glycine copolymer with the weight-average molecular weight of 150,000 are prepared into a blend; and the blank of low-carbon low-alloy steel is subjected to extrusion molding and then is machined into a hollow bone screw, and an inner cavity of the bone screw is filled with a blend of the polylactic acid and the polymaleic anhydride-glycine copolymer, glutathione serving as an antioxidant and sodium hexametaphosphate serving as a complexing agent, wherein the mass ratio of the low-carbon low-alloy steel to the blend is 80:20.

The initial bending strength of the material manufactured for the bone screw in this embodiment is 600 MPa, and after accelerated corrosion in vitro for four weeks, the mass percent of the soluble iron in corrosion products of the iron-based ally is 10 weight percent.

Contrast 1

A blank of as-cast pure iron is hot-rolled into a steel wire rod which then is cold-drawn into an iron wire, and multiple strands of iron wires are stranded to form a suture.

The initial bending strength of the suture is 600 MPa, and after accelerated corrosion in vitro for four weeks, the mass percent of the soluble iron in corrosion products of the iron-based ally is 0.

Contrast 2

Low-carbon low-alloy steel with a carbon content of 0.1 weight percent is prepared into a blank by powder metallurgy, and then the blank is further subjected to thermal treatment; polylactic acid with the weight-average molecular weight of 2,000,000 and the polydispersity index of 1.8 and a polymaleic anhydride-glycine copolymer with the weight-average molecular weight of 150,000 are prepared into a blend; and the blank of low-carbon low-alloy steel is subjected to extrusion molding and then is machined into a hollow bone screw, and an inner cavity of the bone screw is filled with the blend of the polylactic acid and the polymaleic anhydride-glycine copolymer, wherein the mass ratio of the low-carbon low-alloy steel to the blend is 95:5.

The initial bending strength of the material of the bone screw is 650 MPa, and after accelerated corrosion in vitro for three weeks, the mass percent of the soluble iron in the iron-based ally corrosion products of the iron-based ally is 2 weight percent.

Contrast 3

Low-alloy, high-strength steel with an alloy content less than 6 weight percent is cast into a blank, then the blank is subjected to cold drawing to form an ultrafine steel wire with a diameter of 0.2 mm, and then thermal treatment is carried out.

A blank of polylactic acid-co-glycolic acid (PLGA) with the weight-average molecular weight of 100,000 and the polydispersity index of 15 is heated to a molten state; the steel wire which is made into the diameter of 0.2 mm in the above steps is cut into small sections with different lengths; the small sections are arrayed directionally and are added into the molten PLGA blank so as to be used as a reinforcement phase; after condensation and solidification, the molten PLGA blank is extruded into a rod; and the rod is machined into a bone screw 10 as shown in FIG. 1, wherein the mass ratio of the steel wire reinforcement phase 11 to a polylactic acid-glycolic acid phase 12 is 20:80.

The initial bending strength of the material manufactured for the bone screw is 60 MPa, and after accelerated corrosion in vitro for three weeks, the mass percent of the soluble iron in corrosion products of the iron-based ally is 10 weight percent.

It can be seen from the embodiments 1 to 7 and the contrasts 1 to 3 that the absorbable and implantable medical device for internal fixation manufactured in all the embodiments have their initial bending strengths not less than 350 MPa or tensile strengths not less than 400 MPa, so that all the devices have high initial mechanical properties, and are applicable to fixation of the load-bearing position; by the arrangement of the mass ratios of the iron-based alloys to the degradable polymers and their combination modes, the proportion of the insoluble corrosion product in corrosion products of the iron-based alloy is reduced; and the adding of the antioxidant and the complexing agent further reduces the proportion of the insoluble corrosion product in corrosion products of the iron-based alloy, so that the burden on the tissues for metabolizing the corrosion products is relieved.

The above embodiments are merely expressive of several exemplary implementation modes of the present application, and their descriptions are relatively specific and detailed, but may not be deemed as limitations to claims of the present application. It should be noted that ordinary persons skilled in the art also can make a plurality of transformations and improvements without departing from the idea of the present application, and these transformations and improvements shall all fall within the scope of protection of the present application. Therefore, the scope of protection of the patent of the present application shall be based on attached claims.

The invention claimed is:

1. An iron-based alloy absorbable and implantable medical device for internal fixation, comprising:
a substrate of the iron-based alloy absorbable and implantable medical device for internal fixation that comprises an iron-based alloy and a degradable polymer; and
a degradable adhesive;
wherein the substrate has a mass ratio of the iron-based alloy to the degradable polymer that is between 1:4 and 4:1;
wherein the degradable polymer has a weight-average molecular weight that is more than or equal to 150,000 and less than or equal to 3,000,000, and a polydispersity index that is more than or equal to 1 and less than or equal to 6; and
wherein the degradable adhesive is selected from the group consisting of a polyester hot melt adhesive, a polyamide hot melt adhesive, a starch, a cyclodextrin, and a lignin; or wherein the degradable adhesive is a copolymer of at least two monomers selected from the group of monomers that form the polyester hot melt adhesive, the polyamide hot melt adhesive, the starch, the cyclodextrin, and the lignin.

2. An iron-based alloy absorbable and implantable medical device for internal fixation, comprising:
a substrate of the iron-based alloy absorbable and implantable medical device for internal fixation that comprises an iron-based alloy and a degradable polymer; and
a degradable adhesive;
wherein the substrate has a mass ratio of the iron-based alloy to the degradable polymer that is between 1:4 and 1:1;
wherein the degradable polymer has a weight-average molecular weight that is more than or equal to 150,000 and less than or equal to 3,000,000, and a polydispersity index that is more than or equal to 1 and less than or equal to 6;
wherein the degradable adhesive is selected from the group consisting of a polyester hot melt adhesive, a polyamide hot melt adhesive, a starch, a cyclodextrin, and a lignin; or wherein the degradable adhesive is a copolymer of at least two monomers selected from the group of monomers that form the polyester hot melt adhesive, the polyamide hot melt adhesive, the starch, the cyclodextrin, and the lignin.

3. The iron-based alloy absorbable and implantable medical device for internal fixation according to claim 2, further comprising an antioxidant which is selected from the group consisting of butyl hydroxy anisole, butylated hydroxytoluene, tertiary butylhydroquinone, propyl gallate, carotenoid, ubiquinone, glutathione, water-soluble polyphenol, tocopherol, sodium tripolyphosphate, sodium ascorbate, lipoic acid salt and ascorbic palmitate.

4. The iron-based alloy absorbable and implantable medical device for internal fixation according to claim 2, wherein a structural relationship between the iron-based alloy and the degradable polymer is selected from the group consisting of:
the iron-based alloy is distributed in the degradable polymer in a form of a solid or hollow bristle shape, filament shape or rod shape, a stent or a mesh;
the iron-based alloy and the degradable polymer are respectively prepared into layers, and the iron-based alloy layer and the polymer layer are alternated with each other;
the iron-based alloy is stranded on a degradable polymer filament in the form of a filament; and
the iron-based alloy has a groove, a pore, a gap or a hollow inner cavity, and the groove, the pore, the gap or the hollow inner cavity is filled with the degradable polymer.

5. The iron-based alloy absorbable and implantable medical device for internal fixation according to claim 2, wherein the degradable polymer comprises:
a degradable polyester,
a mixture of the degradable polyester and at least one of a degradable polyanhydride, a degradable polyamino acid and a degradable polyphosphate ester, or
a copolymer of at least one monomer forming the degradable polyester and at least one monomer forming the degradable polyanhydride, the degradable polyamino acid or the degradable polyphosphate ester.

6. The iron-based alloy absorbable and implantable medical device for internal fixation according to claim 5, wherein:
the degradable polyester is selected from the group consisting of polylactic acid, polyglycolic acid, poly(ethylene succinate), polycaprolactone, polyhydroxyalkanoate, polyethylene glycol adipate, a polylactic acid-glycolic acid copolymer, a polyhydroxybutyrate-pentanoate copolymer, and copolymers thereof;
the degradable polyanhydride is selected from the group consisting of crosslinked polyanhydride, aromatic polyanhydride, fatty acid polyanhydride, heterocyclic polyanhydride, poly-acyl anhydride, polyamide anhydride, and phosphorus-containing polyanhydrides; and
the degradable polyamino acid is selected from the group consisting of polyglycine, poly-methionine, polythionine, and polyaspartic acid.

7. The iron-based alloy absorbable and implantable medical device for internal fixation according to claim 2, further comprising a complexing agent; wherein the complexing agent comprises a monodentate ligand and/or a polydentate ligand; wherein the monodentate ligand contains a single coordination group; wherein the polydentate ligand contains at least two coordination groups, said at least two coordination groups contain a hydroxyl on polycyclic aromatic hydrocarbon, sulfhydryl, amido, a hetero aromatic group, nitroso, carbonyl, sulpho, a phosphate group or an organic phosphine group.

8. The iron-based alloy absorbable and implantable medical device for internal fixation according to claim 2, wherein the iron-based alloy has a carbon content less than or equal to 2.11 weight percent.

9. The iron-based alloy absorbable and implantable medical device for internal fixation according to claim 2, wherein the device is a bone screw or a suture.

10. The iron-based alloy absorbable and implantable medical device for internal fixation according to claim 2, wherein the initial bending strength is 350 MPa to 600 MPa.

\* \* \* \* \*